US00PP30458P3

(12) United States Plant Patent
Klemm et al.

(10) Patent No.: US PP30,458 P3
(45) Date of Patent: Apr. 30, 2019

(54) ***PELARGONIUM* PLANT NAMED 'KLEPZ17435'**

(50) Latin Name: *Pelargonium zonale*
Varietal Denomination: KLEPZ17435

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,936

(22) Filed: May 23, 2018

(65) Prior Publication Data

US 2018/0343778 P1 Nov. 29, 2018

(30) Foreign Application Priority Data

May 24, 2017 (CH) ..... PBR 17-3146

(51) Int. Cl.
*A01H 5/02* (2018.01)
*A01H 6/42* (2018.01)

(52) U.S. Cl.
USPC ..... Plt./326
CPC ..... *A01H 6/425* (2018.05)

(58) Field of Classification Search
USPC ..... Plt./263.1, 324, 325, 326
See application file for complete search history.

*Primary Examiner* — Susan McCormick Ewoldt
*Assistant Examiner* — Karen M Redden
(74) *Attorney, Agent, or Firm* — Bethany R. Roahrig; Cochran Freund & Young LLC

(57) ABSTRACT

A new *Pelargonium* plant particularly distinguished by white flowers, a mounding habit, and good branching, is disclosed.

1 Drawing Sheet

Genus and species: *Pelargonium zonale.*
Variety denomination: 'KLEPZ17435'.

CROSS REFERENCE TO RELATED APPLICATION

The present application claims priority to Switzerland Plant Variety Protection Application No. 17-3146, as filed on May 24, 2017, the entire contents are herein incorporated by reference for all the application teaches and discloses. A European Community Plant Variety Protection Application was filed on May 30, 2017, Application No. 2017/1441.

BACKGROUND OF THE NEW PLANT

The present invention comprises a new and distinct variety of *Pelargonium*, botanically known as *Pelargonium zonale* and hereinafter referred to by the variety name 'KLEPZ17435'. 'KLEPZ17435' originated from a hand pollination in July 2011 in Stuttgart, Germany between the female proprietary *Pelargonium* variety SUNRISE 'XL Cassandra', also known as 'KLEPZ05139' (unpatented) and the male proprietary *Pelargonium* variety SUNRISE 'Paloma', also known as 'KLEPZ10271' (U.S. Plant Pat. No. 22,664).

Seeds from the cross-combination were obtained and sown and plants were grown for evaluation. A single plant was selected in June 2012 and subsequently named 'KLEPZ17435'. In September 2012 'KLEPZ17435' was first vegetatively propagated in Stuttgart, Germany by vegetative cuttings from branches. 'KLEPZ17435' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. White flowers;
2. Mounding growth; and
3. Good branching.

DESCRIPTION OF THE PHOTOGRAPH

This new *Pelargonium* plant is illustrated by the accompanying photograph which shows an overall view of the plant. The photograph is of an approximately 11 weeks old plant old plant grown in Stuttgart, Germany under glasshouse conditions in June 2016.

The colors shown are as true as can be reasonably obtained by conventional photographic procedures.

DESCRIPTION OF THE NEW VARIETY

The following detailed descriptions set forth the distinctive characteristics of 'KLEPZ17435'. The data which define these characteristics were collected from asexual reproductions carried out in Stuttgart, Germany. Data was collected on plants grown three months after planting in Stuttgart, Germany under a glass covered greenhouse in April 2018. Color references are to The R.H.S. Colour Chart of The Royal Horticultural Society of London (R.H.S.), 5$^{th}$ edition (2007).

Classification:
*Family.*—Geraniaceae.
*Botanical.*—*Pelargonium zonale.*
*Common.*—*Pelargonium.*
*Designation.*—'KLEPZ17435'.

Parentage:
*Female.*—SUNRISE 'XL Cassandra' (unpatented).
*Male.*—SUNRISE 'Paloma' (U.S. Plant Pat. No. 22,664).

Plant:
*Form.*—Bushy and round.
*Habit.*—Upright.
*Height.*—13.0 cm.
*Spread.*—24.0 cm.
*Natural flowering season.*—April to October.
*Propagation type.*—Vegetative cuttings.
*Time to produce a finished flowering plant.*—3 months.
*Time to initiate and develop roots.*—4 weeks.
*Root description.*—White, dense, and fine.

Stems:
*Quantity of stems per plant.*—3 to 4.
*Color.*—RHS 143C.
*Surface texture.*—Sparsely pubescent.
*Stem form.*—Round.
*Diameter.*—0.8 cm to 1.2 cm.
*Length.*—7.0 cm to 12.0 cm.
*Internode length.*—1.2 cm to 2.0 cm.
*Anthocyanin.*—Absent.

Leaves:
*Arrangement.*—Alternate.
*Shape.*—Reniform.
*Apex.*—Round.
*Base.*—Slightly open.
*Margin.*—Crenate.
*Texture* (*both surfaces*).—Sparsely pubescent.
*Length.*—3.5 cm to 6.5 cm.
*Width.*—5.0 cm to 10.0 cm.
*Color.*—Upper surface: RHS 143A. Lower surface: RHS 143B.
*Zonation.*—Absent.
*Petiole.*—Length: 3.5 cm. Diameter: 0.3 cm. Color: RHS 143A. Strength: Moderate.
*Venation pattern.*—Palmate.
*Venation color.*—Upper surface: RHS 143A. Lower surface: RHS 144D.

Inflorescence:
*Lastingness of flowers on the plant.*—6 to 8 days.
*Umbels.*—Quantity of umbels per plant: 5 to 7. Length: 11.0 cm to 12.0 cm. Diameter: 8.0 cm to 9.0 cm.
*Individual florets of the umbel.*—Quantity of florets per umbel: More than 20. Depth: 1.5 cm. Diameter: 4.5 cm.
*Fragrance.*—Absent.

Flower buds:
*Cluster shape.*—Round.
*Cluster size.*—Length: 1.3 cm. Width: 2.0 cm.
*Surface texture.*—Moderately pubescent.
*Bud.*—Height: 0.3 cm to 0.5 cm. Width: 0.4 cm. Shape: Round. Apex: Acute. Base: Obtuse. Margin: Entire. Color: RHS 144A.

Petals:
*Quantity per flower.*—6.
*Shape.*—Spatulate.
*Apex.*—Round.
*Base.*—Obtuse.
*Margin.*—Entire.
*Length.*—2.5 cm.
*Width.*—2.3 cm.
*Texture* (*both surfaces*).—Smooth.
*Color of upper and lower lobes* (*both surfaces*).—RHS NN155C.

Petaloids:
*Quantity per flower.*—2 to 4.
*Shape.*—Mixed.
*Apex.*—Mixed.
*Base.*—Obtuse.
*Margin.*—Entire.
*Length.*—0.1 cm to 1.5 cm.
*Width.*—0.1 cm to 0.6 cm.
*Texture* (*both surfaces*).—Smooth.
*Color* (*both surfaces*).—RHS NN155C.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Moderately pubescent.
*Color.*—Upper surface: RHS 144B. Lower surface: RHS 144A.
*Length.*—1.2 cm.
*Width.*—0.4 cm.

Pedicel:
*Length.*—2.0 cm.
*Diameter.*—0.1 cm.
*Color.*—RHS 144B.
*Surface texture.*—Sparsely pubescent.
*Strength.*—Moderate.

Peduncle:
*Length.*—10.0 cm to 12.0 cm.
*Diameter.*—0.4 cm to 0.5 cm.
*Color.*—RHS 144A.
*Surface texture.*—Sparsely pubescent.
*Strength.*—Moderate.

Reproductive organs:
*Stamens.*—Quantity of stamens per flower: 5 to 7. Anther length: 0.2 cm. Filament length: 0.4 cm. Filament color: RHS NN155C. Pollen amount: Moderate. Pollen color: RHS N172C.
*Pistils.*—Number: 1. Stigma color: RHS NN155A. Style length: 0.3 cm. Style color: RHS 144D. Ovary arrangement: Central. Ovary color: RHS 143A. Ovary diameter: 0.2 cm. Ovary length: 0.5 cm.

Fruit and seed set: None observed.

Disease and pest/insect resistance: None observed.

COMPARISON WITH PARENTAL LINES AND KNOWN VARIETY

'KLEPZ17435' is distinguished from its parents as described in Table 1:

TABLE 1

| Comparison with Partental Lines | | | |
|---|---|---|---|
| Characteristic | 'KLEPZ17435' | Female SUNRISE 'XL Cassandra' | Male SUNRISE 'Paloma' |
| Vigour | Medium | Strong | Medium-compact |
| Peduncle length | Medium | Long | Long |

'KLEPZ17435' can be compared to the commercial variety PAX 'Iceberg', (unpatented). Differences between the two varieties are described in Table 2:

TABLE 2

| Comparison with Similar Variety | | |
|---|---|---|
| Characteristic | 'KLEPZ17435' | Commercial line PAC 'Iceberg' |
| Growth type | Mounding | Uproght, long branches |
| Number of florets | More than 20 | 12 to 15 |
| Branching | Good | Low |

We claim:

1. A new and distinct variety of *Pelargonium* plant named 'KLEPZ17435' as illustrated and described herein.

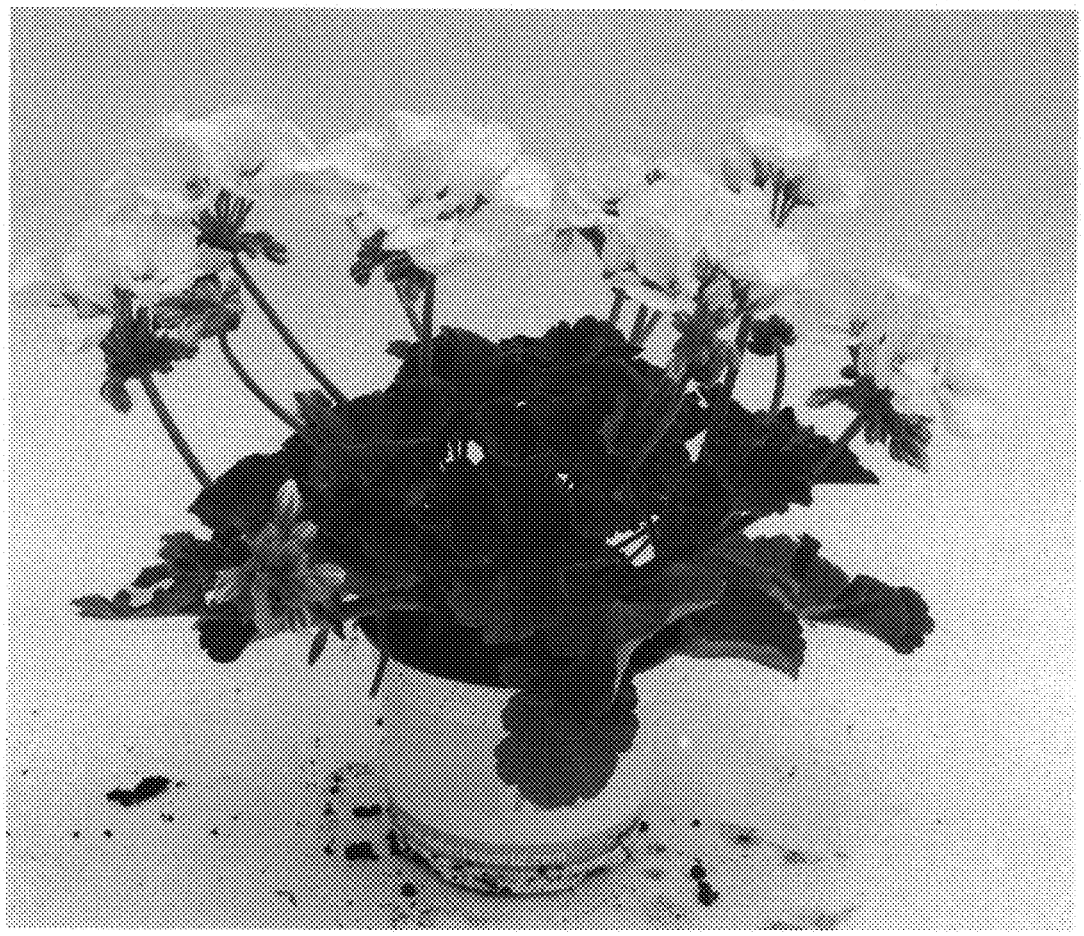

* * * * *